(12) United States Patent
Lally

(10) Patent No.: US 6,787,495 B2
(45) Date of Patent: Sep. 7, 2004

(54) MULTI-PURPOSE REFRACTORY MATERIAL

(76) Inventor: Thomas Joseph Lally, 603 Mallard La., Oak Brook, IL (US) 60523

( * ) Notice: Subject to any disclaimer, the term of this patent is extended or adjusted under 35 U.S.C. 154(b) by 0 days.

(21) Appl. No.: 10/338,425

(22) Filed: Jan. 8, 2003

(65) Prior Publication Data

US 2003/0100435 A1 May 29, 2003

Related U.S. Application Data

(62) Division of application No. 09/602,067, filed on Jun. 22, 2000, now Pat. No. 6,533,821.

(51) Int. Cl.$^7$ ............................ C04B 35/03; C04B 35/04
(52) U.S. Cl. ........................................ 501/111
(58) Field of Search ........................................ 501/111

(56) References Cited

U.S. PATENT DOCUMENTS 6,224,635 B1 * 5/2001 Ricci et al. ............... 623/23.62
6,533,821 B1 * 3/2003 Lally ........................ 623/23.62

* cited by examiner

Primary Examiner—Elizabeth D. Wood

(57) ABSTRACT

The invention discloses a refractory material derived from a mixture comprising: potassium phosphate, magnesium oxide, tricalcium phosphate. The invention relates to a phosphate based refractory material for use in a variety of applications including: casting oven parts, panels, blocks and tiles, bonding parts together, filing in voids in finished castables.

16 Claims, No Drawings

MULTI-PURPOSE REFRACTORY MATERIAL

RELATION TO OTHER APPLICATIONS

The present invention is a divisional of United States patent application entitled, "Bio-Adhesive Composition, Method for Adhering Objects to Bone," application Ser. No. 09/602,067, filed Jun. 22, 2000, now U.S. Pat. No. 6,533,821 issued on Mar. 18, 2003, which is hereby incorporated by reference in its entirety.

BACKGROUND OF THE INVENTION

FIELD OF THE INVENTION

The present invention relates to a multi-purpose refractory material. More specifically, the invention relates to a phosphate based refractory material for use in a variety of applications including: casting oven parts, panels, blocks and tiles, bonding parts together, filing in voids in finished castables. The present invention can also be used as a dental cement suitable for casting impressions and as a refractory mold for teeth, bridges and partials.

DETAILED DESCRIPTION OF THE INVENTION

The present invention is a moldable and castable material, thereby making it an ideal as a refractory. One refractory formulation is comprised of potassium phosphate, magnesium oxide and tricalcium phosphate. The refractory formulation can be adapted to prevent molten metal from sticking to it with the addition of microsilicas. A suitable microsilica is calcium silicate, in particle sizes ranging from approximately 10 microns to 40 microns.

Exemplary formulations of the refractory binder include the following:

| Formulation I: | |
| --- | --- |
| Potassium phosphate (technical grade-30 microns) | 60%* |
| Magnesium oxide (technical grade) | 32%* |
| Tricalcium Phosphate | 8%* |

*Weight percent

The composition of Formulation I can be combined with a filler so that the ultimate mixture contains between 8 and 25 percent by weight of the formulation and 75 to 92 percent by weight of the filler. The variation of binder percentage depends on desired consistency and use of the ultimate mixture.

| Formulation II: | |
| --- | --- |
| Potassium phosphate (technical grade-30 microns) | 61%* |
| Magnesium oxide (technical grade) | 31%* |
| Tricalcium phosphate | 4%* |
| CaSiO$_3$ | 4%* |

*Weight percent

In Formulation II, CaSiO3 is added to reduce build-up of slag when the binder is used in castable formulations. The silicate addition also reduces build-up in refractories which come in contact with molten metals.

| Formulation III: | |
| --- | --- |
| Potassium phosphate (technical grade-30 microns) | 45%* |
| Magnesium oxide (technical grade) | 45%* |
| Tricalcium phosphate | 10%* |

*Weight percent

Formulation III is suitable for casting refractory oven parts, panels, blocks and tiles. In such applications, binder is usually present at between 80–90 weight percent, with the remainder being filler.

| Formulation IV: | |
| --- | --- |
| Potassium phosphate (technical grade-30 microns) | 41%* |
| Magnesium oxide (technical grade) | 41%* |
| Tricalcium phoshate | 9%* |
| Calcium silicate | 9%* |

*Weight percent

Water is added to up to 25 weight percent of the formulation, and preferably 22 to 25 weight percent.

Formulation IV is a multi-purpose refractory grade ceramic cement which can also be used for bonding formed parts together, filling voids in finished castables, and in vivo repair of fractures.

| Formulation V | |
| --- | --- |
| Potassium phosphate (technical grade-30 microns) | 41%* |
| Magnesium oxide (technical grade) | 41%* |
| Tricalcium phosphate | 9%* |
| Silicon dioxide | 9%* |

Formulation V is a dental cement suitable for casting of impressions and as a refractory mold for teeth, bridges and partials.

Some of the formulations disclosed herein incorporate fillers. Exemplary fillers include, but are not limited to, mullite, alumina, sand, clay, volcanic glasses, kyanite, bauxite, aluminum oxide, silicon oxide, chrome oxide, iron oxide, and mixtures thereof.

As disclosed in the materials preparation portion of the bio-adhesive formulation described in the original application (U.S. patent application Ser. No. 09/602,067 filed on Jun. 22, 2000. now U.S. Pat. No. 6.533.821 issued on Mar. 18, 2003) and Incorporated herein, components of the refractory mixture can be dry-mixed and homogenized via a myriad of devices. The material is shipped dry to the ultimate situs of usage and then applied as a slurry once water is added. The amount of water added depends on the workability desired. Generally, and unless additional heat is applied, the exothermic reaction resulting from the slurry formation results in the refractory curing in approximately three hours or less. Use of the refractory can occur within three hours after curing. If outside heat sources are used, for example lasers, the refractory cures within minutes.

The new refractory, with or without the addition of micro-silicates, results in a final green strength of approximately 8500 psi.

While the invention has been described with reference to details of the illustrated embodiments, these details are not intended to limit the scope of the invention as defined in the appended claims.

It should be noted that all the percentages in this application are by weight percent.

What is claimed is:

1. A refractory comprising potassium phosphate, magnesium oxide and tricalcium phosphate.

2. The refractory as recited in claim 1 wherein the potassium phosphate is present in 61 weight percent of refractory, the magnesium oxide is present at 30.5 weight percent, and the tricalcium phosphate is present at approximately 8 weight percent.

3. The refractory formulation as recited in claim 1, which is rendered impervious to molten metal with the addition of calcium silicate.

4. The refractory as recited in claim 3 wherein the calcium silicate is present in a weight percent of approximately 4.1 percent.

5. The refractory as recited in claim 3 wherein the potassium phosphate is present at 61 weight percent of the refractory, the magnesium oxide is present at 30.5 weight percent, the tricalcium phosphate is present at approximately 4.1 weight percent and the calcium silicate is present at approximately 4.1 weight percent.

6. The refractory as recited in claim 1 wherein the potassium phosphate is present at 45 weight percent of the refractory, the magnesium oxide is present at 45 weight percent and the tricalcium phosphate is present at 10 weight percent.

7. The refractory as recited in claim 1, further comprising a compound selected from the group consisting of calcium silicate and silicon dioxide.

8. The refractory as recited in claim 7, wherein the potassium phosphate is present in 41 weight percent of the refractory, the magnesium oxide is present at 41 weight percent, the tricalcium phosphate is present at 9 weight percent and the calcium silicate or silicon dioxide is present at 9 weight percent of the refractory.

9. The refractory as recited in claim 1 wherein the potassium phosphate is between 25–75 weight percent of the refractory.

10. The refractory as recited in claim 1 wherein the potassium phosphate is between 40–65 weight percent of the refractory.

11. The refractory as recited in claim 1 wherein the magnesium oxide is between 15–55 weight percent of the refractory.

12. The refractory as recited in claim 1 wherein the magnesium oxide is between 25–45 weight percent of the refractory.

13. The refractory as recited in claim 1 wherein the tricalcium phosphate is between 0.5–25 weight percent of the refractory.

14. The refractory as recited in claim 1 wherein the tricalcium phosphate is between 3–15 weight percent of the refractory.

15. The refractory as recited in claim 3, wherein the calcium silicate is between 0.1–10 weight percent of the refractory.

16. The refractory as recited in claim 7, wherein the silicon dioxide is between,0.5–10 weight percent of the refractory.

* * * * *